United States Patent [19]

Takahashi et al.

[11] Patent Number: 5,206,160
[45] Date of Patent: Apr. 27, 1993

[54] COMPOSITION CONTAINING BUF-3 AND SUPEROXIDE DISMUTASE AS A CELL CLEAVAGE PROMOTING AGENT

[75] Inventors: Michio Takahashi, No. 1-8-502, Takatsuka-danchi, Takatsukashinden, Matsuod-shi, Chiba-ken; Kunio Shioda, Tokyo; Hiroshiro Shibai, Kawasaki, all of Japan

[73] Assignees: Ajinomoto Company, Inc., Tokyo; Michio Takahashi, Matsudo, both of Japan

[21] Appl. No.: 580,876

[22] Filed: Sep. 11, 1990

[30] Foreign Application Priority Data

Sep. 11, 1989 [JP] Japan ................................ 1-234934

[51] Int. Cl.$^5$ ...................... C12N 9/02; C07K 13/00; A61K 37/36
[52] U.S. Cl. ................................. 435/189; 530/399; 530/350; 514/12; 424/94.4
[58] Field of Search ............... 530/399, 350; 435/189; 514/12; 424/93.4

[56] References Cited

U.S. PATENT DOCUMENTS

4,798,885  1/1989  Mason et al. .................. 530/351
4,997,815  3/1991  Perrine et al. .................. 518/8

FOREIGN PATENT DOCUMENTS

8907135  8/1989  World Int. Prop. O.

OTHER PUBLICATIONS

Linn, Stuart. (1989) Methods in Enzymology, vol. 182, p. 11.
Effect of EDTA on in vitro development of ddY mouse eggs fertilized in vitro, Miyake, N. et al. (1987) Kobe Daigaku Nogakubu Kenkyu Hokoku 17(2) 245–250.
Japanese Journal of Animal Reproduction vol. 36, No. 2, Jun. 1990, pp. 127–133; Rong-zhen, Lu et al: "Activin A (EDF) releases the 'two cell block' of mouse embryos in culture".
Roxus Archives of Developmental Biology vol. 198, 1990, pp. 330–335; Makoto Asashima et al: "Mesodermal induction in early amphibian embryos by activin A (erythroid diferentiation factor)".

Primary Examiner—Amelia Burgess Yarbrough
Assistant Examiner—Lisa T. Bennett
Attorney, Agent, or Firm—Oblon, Spivak, McClelland, Maier & Neustadt

[57] ABSTRACT

A cleavage promoting agent comprising as an effective ingredient at least one of the polypeptides BUF-3, BUF-4 and BUF-5 is useful for the treatment of fertilized or unfertilized ova in order to promote cell division and improve reproduction efficiency.

1 Claim, 2 Drawing Sheets

```
  1                                          10
Gly Leu Glu Cys Asp Gly Lys Val Asn Ile
 11                                          20
Cys Cys Lys Lys Gln Phe Phe Val Ser Phe
 21                                          30
Lys Asp Ile Gly Trp Asn Asp Trp Ile Ile
 31                                          40
Ala Pro Ser Gly Tyr His Ala Asn Tyr Cys
 41                                          50
Glu Gly Glu Cys Pro Ser His Ile Ala Gly
 51                                          60
Thr Ser Gly Ser Ser Leu Ser Phe His Ser
 61                                          70
Thr Val Ile Asn His Tyr Arg Met Arg Gly
 71                                          80
His Ser Pro Phe Ala Asn Leu Lys Ser Cys
 81                                          90
Cys Val Pro Thr Lys Leu Arg Pro Met Ser
 91                                         100
Met Leu Tyr Tyr Asp Asp Gly Gln Asn Ile
101                                         110
Ile Lys Lys Asp Ile Gln Asn Met Ile Val
111
Glu Glu Cys Gly Cys Ser
```

*FIG. 1*

```
  1                                          10
Gly Leu Glu Cys Asp Gly Arg Thr Asn Leu
 11                                          20
Cys Cys Arg Gln Gln Phe Phe Ile Asp Phe
 21                                          30
Arg Leu Ile Gly Trp Asn Asp Trp Ile Ile
 31                                          40
Ala Pro Thr Gly Tyr Tyr Gly Asn Tyr Cys
 41                                          50
Glu Gly Ser Cys Pro Ala Tyr Leu Ala Gly
 51                                          60
Val Pro Gly Ser Ala Ser Ser Phe His Thr
 61                                          70
Ala Val Val Asn Gln Tyr Arg Met Arg Gly
 71                                          80
Leu Asn Pro Gly Thr Val Asn Ser Cys Cys
 81                                          90
Ile Pro Thr Lys Leu Ser Thr Met Ser Met
 91                                         100
Leu Tyr Phe Asp Asp Glu Tyr Asn Ile Val
101                                         110
Lys Arg Asp Val Pro Asn Met Ile Val Glu
111
Glu Cys Gly Cys Ala
```

*FIG. 2*

COMPOSITION CONTAINING BUF-3 AND SUPEROXIDE DISMUTASE AS A CELL CLEAVAGE PROMOTING AGENT

BACKGROUND OF THE INVENTION

1. Field of the Invention

The present invention relates to a cleavage (cell division) promoter, as well as a fertilized or unfertilized ovum treated with the cleavage promoter, and methods for promoting cell division and increasing embryonic selection and shortening pregnancy.

2. Discussion of the Background

Reproduction in higher animals starts with the fusion of the gametes, followed by a definite period inherent to each species, the so-called pregnancy, and finally the delivery (hatching) of the offspring. The reproduction efficiency does not naturally reach 100%. This means that not all contacts between ovulated ova and sperm cells will actually lead to delivery, also defined as embryonic selection.

The reproduction efficiency is 30% or less in humans and approximately 70% in livestock such as swine, bovine etc. Another natural limitation of development and breeding of livestock is the pregnancy period being definite and characteristic for each species.

Improvement in embryonic selection and shortening of pregnancy period would be therefore of great industrial interest, particularly in the field of the livestock industry. On the other hand, the practical and scientific importance of in vitro fertilization for producing transgenic animals, fertilizing externally, etc. has steadily increased. However, up to the present invention success and recovery of in vitro fertilizing experiments have been poor due to insufficient preserving and unefficient development of fertilized or unfertilized ova.

Thus, there remains a need for cell division promoters or cleavage promoters capable of improving the rate of embryonic selection and in vitro fertilization and capable of shortening the pregnancy period.

SUMMARY OF THE INVENTION

Accordingly, it is one object of the present invention to provide novel cell division or cleavage promoters.

It is another object to provide agents capable of improving the rate of embryonic selection and in vitro fertilization, and shortening the pregnancy period.

It is another object to provide a method for promoting cell division or cleavage.

It is another object to provide a method for improving embryonic selection and in vitro fertilization and shortening the pregnancy period.

It is another object to provide fertilized or unfertilized ova which have been treated with a cell division or cleavage promoter.

It is another object to provide fertilized or unfertilized ova which have been treated with a cell division or cleavage promoter, which is capable of improving embryonic selection and in vitro fertilization and shortening the pregnancy period.

These and other objects, which will become apparent in the course of the following detailed description, have been acheived by the inventors' discovery that any of the polypeptides BUF-3, BUF-4 and BUF-5 is effective for promoting cell division.

Thus, the present invention provides a cleavage promoting agent comprising as an effective ingredient at least one of the polypeptides BUF-3, BUF-4 and BUF-5, as well as a fertilized ovum or an ovum treated with the cleavage promoter and a method for promoting cleavage by treating an ovum with such an agent.

According to one embodiment of this invention, these polypeptides BUF-3, BUF-4 and BUF-5 can be used in combination with superoxide dismutase (SOD) and/or ethylenediaminetetraacetic acid (EDTA) as an auxiliary agent for effectively promoting cell division.

In the following description, the agent which promotes cell division is designated as a cell division promoter or cleavage promoter, respectively.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 illustrates the amino acid sequence of monomer A; and

FIG. 2 illustrates the amino acid sequence of monomer B.

DETAILED DESCRIPTION OF THE PREFERRED EMBODIMENTS

In fertilized ova in most mammals, it is known that development stops at a definite period of time, when incubated in vitro; in the case of a mouse, it is known that in vitro development is discontinued at the two-cell phase.

In such a case, when at least one of polypeptides BUF-3, BUF-4 and BUF-5 is administered, cleavage can be accelerated as follows. Where a fertilized ovum collected from a mated mouse is incubated in Whitten's medium, a suitable amount of the cleavage promoter of the present invention is added to the medium, whereby transfer to the four-cell phase and further to the morula phase can be promoted. When the thus-obtained embryo is transplanted to an expedient mother, normal development is observed through pregnancy and delivery. This method is also applicable to other animals.

Fertilized ova or ova treated with the cleavage promoter of the present invention can suitably be those originating from fish, birds, or mammals, in more detail, originating from cattle, swine, sheep, goat, horse, rat, dog, cat or humans. The fertilized ova or ova may be delivered (hatched) as they are, or may also be lyophilized.

The physicochemical properties of the polypeptides BUF-3, BUF-4 and BUF-5 are as follows.

(1) Physicochemical properties of polypeptide BUF-3 (hereafter referred to as BUF-3)

(a) Structure: homodimer of monomer A (cf. FIG. 1)

(b) Molecular weight: $16\pm1$ kd as monomer (in the presence of 1.0% mercaptoethanol, SDS-electrophoresis) $25\pm1$ kd as homodimer (in the absence of mercaptoethanol, SDS-electrophoresis)

(c) Isoelectric point: pI $6.3\pm0.2$ (chromatofocusing) pI 7.3 (isoelectric point electrophoresis)

(d) pH stability: stable in a pH range of from 2.0 to 10.0

(e) Heat stability: It is stable with heating at 60° C. for 60 minutes.

f) Stability in organic solvents: It is stable in lower alcohols and acetonitrile.

(g) Resistance to protease: It is completely inactivated by treatment with pronase.

(h) Amino acid sequence: Amino acid sequence of monomer A is shown in FIG. 1.

(2) Physicochemical properties of polypeptide BUF-4 (hereafter referred to as BUF-4)

(a) Structure: heterodimer of monomer A and monomer B (cf. FIGS. 1 and 2)

(b) Molecular weight: both monomer A and monomer B: $16 \pm 1$ kd (in the presence of 1.0% mercaptoethanol, SDS-electrophoresis) $25 \pm 1$ kd as heterodimer (in the absence of mercaptoethanol, SDS-electrophoresis).

(c) Isoelectric point: pI $7.3 \pm 0.5$ (isoelectric point electrophoresis)

(d) pH stability: stable in a pH range of from 2.0 to 10.0

(e) Heat stability: It is stable with heating at 65° C. for 60 minutes.

(f) Stability in organic solvents: It is stable in lower alcohols and acetonitrile.

(g) Resistance to protease: It is completely inactivated by treatment with pronase.

(h) Amino acid sequence: Amino acid sequences of monomer A and monomer B are shown in FIG. 1 and FIG. 2, respectively.

(3) Physicochemical properties of polypeptide BUF-5 (hereafter referred to as BUF-5)

(a) Structure: homodimer of monomer B (cf. FIG. 2.)

(b) Molecular weight: $16 \pm 1$ kd as monomer (in the presence of 1.0% mercaptoethanol, SDS-electrophoresis) $25 \pm 1$ kd as homodimer (in the absence of mercaptoethanol, SDS-electrophoresis)

(c) Isoelectric point: pI $7.3 \pm 0.5$ (isoelectric point electrophoresis)

(d) pH stability: stable in a pH range of from 2.0 to 10.0

(e) Heat stability: It is stable with heating at 65° C. for 60 minutes.

(f) Stability in organic solvents: It is stable in lower alcohols and acetonitrile.

(g) Resistance to protease: It is completely inactivated by treatment with pronase.

(h) Amino acid sequence: Amino acid sequence of monomer B is shown in FIG. 2.

For the purpose of the present invention, the terms BUF-3, BUF-4 and BUF-5 include all biological equivalents of these substances as long as they have cleavage promoting activity, even if they do not have quite the same amino acid sequences as shown in FIGS. 1 and 2.

That is, the BUF-3, BUF-4 and BUF-5 of the present invention also include polypeptides having a structure in which one or more amino acids in the amino acid sequence shown in FIG. 1 or FIG. 2 are replaced by other amino acids, a substance having a structure in which one or more amino acids in the amino acid sequence are added to the N-terminus and/or C-terminus, and furthermore, a substance in which in the above stated amino acid sequence one or more amino acids are deleted from the N-terminus or C-terminus.

BUF-3 is used as a purified polypeptide, which is assayed by the differentiation induction activity on mouse Friend leukemia cells FS-5 as an index. It is already known that BUF-3 exhibits various physiological activities. For example, BUF-3 is a useful substance which also exhibits, in addition to an activity of differentiating and maturing mouse leukemia cells into normal cells (Japanese Patent Application Laid-Open Nos. 234097/1987 and 24070/1987), an effect of treating anemia (Japanese Patent Application Laid-Open Nos. 234097/1987 and 24070/1987) and an activity of secreting follicle stimulating hormone (Nature, vol. 321, pp. 776-779 (1986)).

BUF-3 is also called EDF (Erythroid Differentiation Factor) or FRP (FSH Releasing Protein). In the present invention, the term BUF-3 which has been in common use is used throughout the specification.

On the other hand, it has already been reported that BUF-4 exhibits the activity of secreting follicle stimulating hormone (Vale, W., River, J., Vaughan, J., McClintock, R., Corrigan, A., Woo, W., Karr, D. and Spiess, T., Nature, vol. 321, pp. 776-777 (1986)).

BUF-4 is also called activin, but the term BUF-4 is used in the present invention.

BUF-5 is a substance disclosed in Japanese Patent Application Laid-open No. 119679/1988.

As described above, it is already known that BUF-3, BUF-4 and BUF-5 have the activity of releasing follicle stimulating hormone and the like, but no report has been made on any cleavage promoting activity.

In the following, methods for producing BUF-3, BUF-4 and BUF-5 having cleavage promoting activity are described.

BUF-3 can be produced by cell culture of malignant leukemia cells or by recombinant DNA techniques.

Regarding cell culture, human malignant monocytes capable of producing BUF-3 are exemplified by human leukemia cells or human myeloid cells which are artificially rendered malignant, and specific examples include human chronic myeloid leukemia cells (U-937 ATCC CRL 1593, Int. J. Cancer, vol. 17, p. 565 (1976), K562, Blood, vol. 45, p. 321 (1975)), acute monocytic leukemia cells (THP-1, Int. J. Cancer, vol. 26, pp. 171-176 (1980)). Of course, human leukemia cells other than those described above may be used as long as BUF-3 is produced. A specific differentiation inducer is a substance that can differentiate and induce malignant monocytes into macrophage and monocytes of granulocytes as the contact with malignant monocytes and at the same time, can produce BUF-3. Specific examples of the specific differentiation inducers include actinomycin D, mitomycin C, concanavalin A and phorbol ester (TPA), etc.

To produce BUF-3 of the present invention, malignant monocytes are cultured in the co-presence of at least one or more of the aforesaid specific differentiation inducers, whereby BUF-3 is produced in the culture solution (extracellularly).

For culturing malignant monocytes a conventional medium for culturing animal cells is used. A preferred example is Rosewell Park Memorial Institute 1640 medium (hereafter simply referred to as RPMI-1640).

Culture of malignant monocytes is carried out generally at a cell density of 1 to $5 \times 10^6$/ml at 35° to 38° C. in a carbon dioxide gas flow of 4 to 6% while gently agitating. The specific differentiation inducer may be added at an initial state of the culture or during the course of the culture. The amount added may vary depending upon the kind of the differentiation inducer and is 0.1 to 10 µg/ml in the case of actinomycin D, mitomycin C, etc. and 1 to 500 ng/ml in the case of TPA. When cultured for 1 to 5 days, BUF-3 is accumulated in the culture medium.

In addition to the cleavage activity, BUF-3 has a differentiation induction activity on Friend leukemia virus cells F5-5 (Bibl. Haemst., vol. 43, p. 37 (1976)). Therefore, by using this activity, a qualitative and quantitative assay for BUF-3 can be performed. The assay using F5-5 can be made in accordance with the method described in *Proc. Natl. Acad. Sci.*, vol. 71, p. 98 (1975). The activity is expressed in terms of activity per 1.0 ml of stock solution by using the reciprocal number of dilution of the stock solution of samples at which differentiation of F5-5 cells is clearly confirmed. When BUF-3 is produced by the method of the present invention, the culture medium indicates an activity of 4 to 1000 units/ml. Thus, the desired BUF-3 is produced.

Details of this method are described in Japanese Patent Application Laid-Open Nos. 234097/1987 and 24070/1987.

Alternatively, BUF-3 can also be produced by recombinant DNA techniques, that is, culturing eucaryotic cells (specifically IFO-50146, etc.) transformed by a plasmid containing a gene encoding BUF-3, i.e., monomer A and producing BUF-3 in the culture medium (Japanese Patent Application No. 210810/1987; Masahiro Murata, Kazuya Onomichi, Yuzuru Eto, Hiroshiro Shibai and Masami Muramatsu, BIOCHEMICAL AND BIOPHYSICAL RESEARCH COMMUNICATIONS, vol. 151 (1), pp. 230-235 (1988)).

The production of BUF-4 and BUF-5 is carried out in a manner similar to the production of BUF-3 by recombinant DNA engineering and hence, only its outline is described below.

To produce BUF-4, eucaryotic cells transformed by a plasmid containing a gene encoding BUF-4, i.e., monomer A and monomer B may be cultured in medium and BUF-4 is produced in the culture medium (Japanese Patent Application Laid-Open No. 119679/1988).

To produce BUF-5, eucaryotic cells transformed by a plasmid containing a gene encoding BUF-5, i.e., monomer B may be cultured in medium and BUF-5 is produced in the culture medium (Japanese Patent Application Laid-open No. 119679/1988).

Now the thus produced BUF-3, BUF-4 or BUF-5 can be purified in a manner similar to the conventional purification of a polypeptide. Crude polypeptide standard can be obtained by, for example, concentrating the culture medium, salting-out the polypeptides from the concentrate and then performing ion exchange chromatography using an anionic exchanger. By hydrophobic chromatography or chromatofocusing of the crude standard, almost all protein impurities can be removed. By using both chromatographies in combination, the purification degree can further be increased. The thus-purified standard product can further be purified by performing high efficiency gel filtration or ion exchange chromatography through reverse phase high performance liquid chromatography (HPLC) or FPLC (manufactured by Pharmacia, Fast Protein Peptide Polynucleotide Liquid Chromatography) system equipped with a Super Rose or Mono QHR5/5 column.

Independent from the conventional purification of polypeptide as described above, BUF-3, BUF-4 and BUF-5 may also be purified by the method of purification using organic solvents containing organic acids in a definite concentration which was developed by the present inventors (Japanese Patent Application No. 131268/1988). According to this method, culture supernatant including BUF-3 is crudely purified by using a sequence of concentration, ammonium sulfate precipitation and dialysis against tris-hydrochloride buffer system. The crude BUF-3 solution obtained by the above-mentioned method is treated with 0.1-3.0M potassium thiocyanate, 25-95% acetonitrile containing 0.05-1.0% TFA (trifluoroacetate) and adjusted to pH 1.0-3.0 by adding 1.0-30.0% TFA.

By this procedure, almost all of contaminant protein, such as bovine serum albumin, is precipitated and removed by centrifugation. However, more than 80% of BUF-3 remains in the supernatant due to its characteristic hydrophobicity. The specific activity of BUF-3 is remarkably increased by this procedure.

Finally, BUF-3 is purified to homogeneity by applying sequential 3-step reverse phase HPLC. This method is also applicable to BUF-4 and BUF-5.

The BUF-3, BUF-4 and BUF-5 in accordance with the present invention can be used alone or in a combination of two or all three.

The content of the BUFs in the cleavage promoting agent of the present invention is 0.0001 to 100 wt %, preferably 0.1 to 99 wt %, in total, based on the weight of the cleavage promoting agent.

The terms BUFs collectively refers to BUF-3, BUF-4 and BUF-5.

The cleavage promoting agent of the present invention comprising the BUFs of the present invention as an effective ingredient may also contain an appropriate amount of superoxide dismutase (hereinafter referred to as SOD) and/or ethylenediaminetetraacetic acid (hereinafter referred to as EDTA) as an auxiliary agent. These auxiliary agents improve the function of promoting cleavage synergistically.

The content of SOD in the cleavage promoting agent of the present invention is not limited, but is usually 0.0001 to 99.0 wt. %, based on the weight of the cleavage promoting agent. The origin of SOD is not limited. Therefore SOD originating from human, dog, bovine, bacteria and others can be used.

The content of EDTA in the cleavage promoting agent of the present invention is not limited, but is usually 0.0001 to 99.0 wt. %, based on the weight of the cleavage promoting agent.

The cleavage promoting agent of the present invention may also contain a stabilizer such as serum albumin etc., an excipient such as mannitol etc. and other common, pharmacological additives.

Using the cleavage promoter of the present invention, fertilized ova of various animals can be treated. Even though ova are not fertilized, the ova may be fertilized after treating with the cleavage promoter in accordance with the present invention.

For treating the fertilized ovum or ovum with the cleavage promoter of the present invention, the cleavage promoter of the present invention is dissolved in physiological saline or a Tris buffer solution etc. to contain the BUFs in a final concentration of 0.01 ng/ml to 100 $\mu$g/ml, preferably 0.1 ng/ml to 1.0 $\mu$g/ml, and the fertilized ovum or ovum is then dipped in the resulting solution for 10 minutes to 7 days, preferably for an hour to 2 days.

Also, when SOD and/or EDTA as an auxiliary agent is present in combination with BUFS, the cleavage promoter of the present invention is dissolved in physiological saline or a Tris buffer solution etc. to contain SOD in a final concentration of 0.01 $\mu$g/ml to 1.0 mg/ml or to contain EDTA in a final concentration of 0.1 ng/ml to 10 mg/ml.

The temperature of the solution for the treatment is generally 0° C. to 45° C., preferably about 37° C.

The above conditions are generally set forth, but the present invention is not necessarily restricted to these conditions.

In addition to the dipping method described above, the micro injection method or the like may also be used as the method for treatment.

Other features of the invention will become apparent in the course of the following descriptions of exemplary embodiments which are given for illustration of the invention and are not intended to be limiting thereof.

EXAMPLES

Example 1

Animal and Recovery of Fertilized Ovum

Three to four week old ICR strain mice (Japan Charles River Co. Ltd.) were used as test animals which had been fed under the condition of 14L10D (under light conditions from 5:00 AM to 7:00 PM). Pregnant mare serum gonadotropin (hereafter simply referred to as PMSG) was administered to the female mice in a dose of 5 I.U. Forty-eight hours after the administration, human chorionic gonadotropin (hereafter simply referred to as hCG) was administered in a dose of 5 I.U.

The-thus treated female mice were mated, and the fertilized ova were collected. At 10:00 AM on Day 1 of pregnancy (19 hours after administration of hCG), the heads of mice were cut off and the oviducts were withdrawn.

The fertilized ova were recovered from the oviducts in Whitten's medium (pH 7.0) (hereafter simply referred to as WM-B) containing bovine serum albumin (hereafter referred to as BSA; manufactured by Boehringer Mannheim Inc., 735078).

The fertilized ova were then treated with hyaluronidase solution (150 units/ml in WM-B) until the cumulus mass was removed (room temperature, one minute or less). Thereafter, the ova having the second polar body or both pronuclea were selected and washed 5 times with WM-B.

Example 2

Incubation of Fertilized Ova.

BUF-3 was dissolved in WM-B containing HEPES buffer (SIGMA Inc., No. H-0264) in concentrations of 0.1 ng/ml, 1.0 ng/ml and 10.0 ng/ml (hereafter simply referred to as BUF-3 solution). Each solution was used in the following run.

After 15 to 25 fertilized ova were suspended in 1 ml of WM-B or BUF-3 solution, incubation was performed at 37° C. for 48 hours in 5% $CO_2$, 5% $O_2$ and 90% $N_2$.

BUF-3 was added for the latter 24, hours and its concentration-dependent effect was examined. As the result, only 16.7% of the fertilized ova were transferred to the four-cell phase in the group with no added BUF-3, whereas 42.9% and 83.1% of the fertilized ova were transferred to the four-cell phase in the group with 0.1 ng/ml of added BUF-3 and the group with 1.0 ng/ml of added BUF-3, respectively. The details are shown in Table 1.

TABLE 1

| Concentration of BUF-3 | Rate of Transfer to Four-Cell Phase (%) |
|---|---|
| 0 | 16.7 |
| 0.1 ng/ml | 42.9 |
| 1.0 ng/ml | 83.1 |

Example 3

Transplantation of Embryo

Embryos transferred to the four-cell phase by the treatment of BUF-3 were transplanted to a female mouse on Day 2 of pseudopregnancy. On Day 18 after the transplantation, the mouse delivered babies.

Example 4

Animal and Recovery of Fertilized Ova

Mice used in this study were CD-1 (Charles River, Japan) and DBA/2JJ (Clea, Japan Inc.). Mice of every strain were held under the condition of 12L-12D (lights on 0700-1900 hr). Female mice were superovulated at 4-5 weeks of age by s.c. injection of 5 I.U. pregnant mare's serum gonadotrophin (PMSG), followed 48 hrs. later by s.c. injection of 5 I.U. human chorionic gonadotrophin (hCG) and were mated with males of the respective strains after hCG injection.

The fertilized ova were collected about 17 hours after hCG injection. Then the cumulus cells were removed by treatment with hyaluronidase (150 unit/ml). The fertilized ova identified by the presence of a second polar body and two pronuclei were used in the following experiments.

Example 5

Incubation of Fertilized Ova.

Ten to twenty fertilized ova were placed in about 0.5 ml of Whitten's Medium (WM), pH 7.2, (Whitten, 1971), containing 3 mg/ml of bovine serum albumin and incubated in an atmosphere of 5% $CO_2$ in air at 37° C. until 72 hours from the addition of hCG.

The total culture period was 72 hours, and the rate of development of the fertilized ova to the 4-cell (after 48 hours of culture) or morula stage (after 72 hours of culture) was evaluated.

Example 6

Synergistic Effect Originating from a Combination of BUF-3 and SOD on CD-1 Mouse Ova.

The fertilized ova were cultured in the presence of (i) 1 ng/ml of BUF-3 or (ii) 1 ng/ml of BUF-3 and 75 µg/ml of SOD (produced from bovine erythrocytes, Sigma, S-2515).

Then, the rate of development to the 3-4 cell stage and the morula stage in each fraction was evaluated.

As shown in Tables 2 and 3, the rate of development of fertilized ova cultured in the presence of only BUF-3 was significantly increased.

Also, a further statistically significant effect was found in the fraction cultured in the presence of a combination of BUF-3 and SOD.

The control is the fraction without adding either BUF-3 or SOD.

TABLE 2

| | Rate of Development to 3-4 Cell Stage (%) |
|---|---|
| Control | 28.6 |
| BUF-3 | 50.0 |
| BUF-3 + SOD | 81.1 |

TABLE 3

| | Rate of Development of Morula Stage (%) |
|---|---|
| Control | 20.3 |
| BUF-3 | 55.0 |
| BUF-3 + SOD | 86.5 |

Example 7

Synergistic Effect Originating from a Combination of BUF-3 and EDTA on DBA/2JJ mouse Ova.

The fertilized ova were cultured in the presence of (i) 2.5 ng/ml of BUF-3 or (ii) 2.5 ng/ml of BUF-3 and 3.15 μg/ml of EDTA (Sigma, ED2SS).

Then the rate of development to the four-cell stage and the morula stage in each fraction was evaluated.

As shown in Tables 4 and 5, the rate of development of fertilized ova cultured in the presence of only BUF-3 was significantly increased.

Also, a further statistically significant effect was found in the fraction treated by a combination of BUF-3 and EDTA. The control is the fraction without adding either BUF-3 or EDTA.

TABLE 4

| | Rate of Development to Four-Cell Stage (%) |
|---|---|
| Control | 11.1 |
| BUF-3 | 50.7 |
| BUF-3 + EDTA | 77.4 |

TABLE 5

| | Rate of Development to Morula Stage (%) |
|---|---|
| Control | 0 |
| BUF-3 | 21.1 |
| BUF-3 + EDTA | 64.8 |

Effects

By the use of the cleavage promoter of the present invention, the rate of in vitro fertilization in animals and mammals, such as livestock can be markedly improved.

Accordingly, the promoter of the present invention is considered to be an extremely useful substance in the field of the livestock industry.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A cleavage promoting agent, comprising BUF-3 and superoxide dismutase.

* * * * *

UNITED STATES PATENT AND TRADEMARK OFFICE
CERTIFICATE OF CORRECTION

PATENT NO. : 5,206,160
DATED : April 27, 1993
INVENTOR(S) : Michio Takahashi et al.

It is certified that error appears in the above-identified patent and that said Letters Patent is hereby corrected as shown below:

On the title page, [75],

The inventor's information is incorrect, should read:

--Michio Takahashi, Matsudo; Kunio Shiota, Tokyo; Hiroshiro Shibai,

Kawasaki, all of Japan--

Signed and Sealed this

Fourth Day of January, 1994

*Attest:*

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,206,160
DATED : April 27, 1993
INVENTOR(S) : Michio Takahashi, et. al.

It is certified that error appears in the above-indentified patent and that said Letters Patent is hereby corrected as shown below:

Column 2, line 67, "f)" should read --(f)--.

Column 4, line 33, "Blood" should read --*Blood*--.

Column 7, line 12, after "Ovum", insert --.--.

Column 8, line 3, after "Embryo", insert --.--;
line 11, after "Ova", insert --.--.

Signed and Sealed this

Twentieth Day of September, 1994

Attest:

BRUCE LEHMAN

Attesting Officer

Commissioner of Patents and Trademarks